United States Patent
Morimoto et al.

[11] Patent Number: 5,943,914
[45] Date of Patent: Aug. 31, 1999

[54] MASTER-SLAVE MICROMANIPULATOR APPARATUS

[75] Inventors: Alan K. Morimoto; David M. Kozlowski, both of Albuquerque, N.Mex.; Steven T. Charles, Germantown, Tenn.; James A. Spalding, Springfield, Ky.

[73] Assignee: Sandia Corporation, Albuquerque, N.Mex.

[21] Appl. No.: 08/827,144

[22] Filed: Mar. 27, 1997

[51] Int. Cl.[6] .................... B25J 3/00; B25J 7/00; G05G 11/00
[52] U.S. Cl. .................... 74/479.01; 414/2; 414/3; 414/5; 901/2; 74/480 R
[58] Field of Search .................... 414/2, 3, 5; 901/2; 74/479.01, 480 R; 92/61, 75

[56] References Cited

U.S. PATENT DOCUMENTS

| | | | |
|---|---|---|---|
| 3,832,852 | 9/1974 | Schmucker | 60/546 |
| 4,448,498 | 5/1984 | Muller et al. | 350/516 |
| 4,506,154 | 3/1985 | Scire | 250/442.1 |
| 4,722,056 | 1/1988 | Roberts et al. | 364/413 |
| 4,805,543 | 2/1989 | Schwab et al. | 108/20 |
| 5,116,180 | 5/1992 | Fung et al. | 414/5 |
| 5,193,963 | 3/1993 | McAffee et al. | 414/5 |
| 5,332,181 | 7/1994 | Schweizer et al. | 248/123.1 |
| 5,351,925 | 10/1994 | Druais | 248/325 |
| 5,359,417 | 10/1994 | Müller et al. | 356/375 |
| 5,382,885 | 1/1995 | Salcudean et al. | 318/568.11 |
| 5,389,849 | 2/1995 | Asano et al. | 310/323 |
| 5,402,801 | 4/1995 | Taylor | 128/898 |
| 5,410,638 | 4/1995 | Colgate et al. | 395/99 |
| 5,445,166 | 8/1995 | Taylor | 128/897 |
| 5,476,357 | 12/1995 | Arai | 414/729 |
| 5,762,458 | 6/1998 | Wang et al. | 414/1 |
| 5,784,542 | 7/1998 | Ohm et al. | 395/95 |

FOREIGN PATENT DOCUMENTS

| | | | |
|---|---|---|---|
| 3-73282 | 3/1991 | Japan | 414/5 |
| 2185593 | 7/1987 | United Kingdom | 414/2 |

*Primary Examiner*—John A. Jeffery
*Assistant Examiner*—William C Joyce
*Attorney, Agent, or Firm*—V. Gerald Grafe; Andrew Abeyta

[57] ABSTRACT

An apparatus based on precision X-Y stages that are stacked. Attached to arms projecting from each X-Y stage are a set of two axis gimbals. Attached to the gimbals is a rod, which provides motion along the axis of the rod and rotation around its axis. A dual-planar apparatus that provides six degrees of freedom of motion precise to within microns of motion. Precision linear stages along with precision linear motors, encoders, and controls provide a robotics system. The motors can be positioned in a remote location by incorporating a set of bellows on the motors and can be connected through a computer controller that will allow one to be a master and the other one to be a slave. Position information from the master can be used to control the slave. Forces of interaction of the slave with its environment can be reflected back to the motor control of the master to provide a sense of force sensed by the slave. Forces import onto the master by the operator can be fed back into the control of the slave to reduce the forces required to move it.

13 Claims, 12 Drawing Sheets

MASTER-SLAVE MICROMANIPULATOR APPARATUS

GOVERNMENT RIGHTS

The present invention was made with United States Government support under Contract No. DE-AC04-94AL85000 awarded by the U.S. Department of Energy. The Government has certain rights in this invention.

CROSS-REFERENCE TO RELATED APPLICATIONS

Not applicable.

BACKGROUND OF THE INVENTION

The present invention relates to a micromanipulator and a controller therefor, with six degrees of freedom, for enhanced precision positioning.

Most conventional X-Y stages are built in combination to provide multiple axes of motion and do not have coordinated axes. In other words, many commercial manufacturers stack one linear stage in the X direction upon a second linear stage in a Y direction and a third linear stage in a Z direction, in order to provide three degrees of freedom. These conventional systems do not provide software controls to allow the user to move the stages simultaneously, in order to get more than just individual joint-type motions. Coordinated motion is especially important when attempting to produce something as complex as drawing a circle on a piece of paper. As a non-limiting example, most people understand the principles behind an Etch-a-Sketch, which is controlled with two knobs, one for each of the X and Y directions. It is very difficult to provide a circle type motion with an Etch-a-Sketch because both the X and the Y axes must be coordinated. This is the type of motion that the present invention simplifies and provides. Also, the present invention not only controls the position, but controls velocity and force as well.

SUMMARY OF THE INVENTION

In accordance with the present invention, there is provided an apparatus and method for a dual stage coordinated X and Y and position and orientation output for use as a master-slave micromanipulator. The coordinated X-Y stage with four degrees of freedom comprises a first planar structure comprising a first X and first Y controlled set, a second planar structure comprising a second X and second Y controlled set wherein the second planar structure is stacked on top of the first planar structure, an arm gimbaled to the first planar structure and gimbaled to the second planar structure and a head affixed to the arm comprising a coordinated X and Y position and orientational output. The present invention further comprises a fifth degree of freedom, the fifth degree of freedom comprising structure for movement along the axis of the arm. The apparatus of the present invention further comprises a sixth degree of freedom of motion; the micromanipulator has six degrees of freedom of motion. The sixth degree of freedom can comprise rotation about the axis of the arm. The first planar structure can comprise a top plane float.

The micromanipulator comprises a master dual planar structure comprising a first coordinated and simultaneous X and Y and orientational output, a slave dual planar structure comprising a second coordinated X and Y and orientational output and an apparatus for mimicking and an apparatus for scaling down the first coordinated X and Y and orientational output to the second coordinated X and Y and orientational output. The master-slave design translates, for example, centimeter movements of the master into micrometer movements of the slave. The first coordinated output can comprise a first gimbaled arm and the second coordinated output can comprise a second gimbaled arm. The apparatus further comprises structure for movement along an axis of the first gimbaled arm and the apparatus for mimicking and the apparatus for scaling further comprise scaling and mimicking the movement along an axis of the second gimbaled arm. The apparatus further comprises a structure for rotation about the axis of the first gimbaled arm and the apparatus for mimicking and the apparatus for scaling further comprise scaling and mimicking the rotation along an axis of the second gimbaled arm. The apparatus for mimicking comprises a push—push operation micromanipulator. The push—push apparatuses comprise hydraulic apparatuses. The apparatus for mimicking can comprise a member from the group consisting of direct drive motors, drive screws, lead screws, ball screws, and combinations thereof. One advantage of the present invention is its small size and ability to locate the power sources in a remote location. The apparatus for scaling can comprise a computer. The apparatus further comprises a feedback loop for sending a signal from the second gimbaled arm to the first gimbaled arm when the second gimbaled arm contacts a predetermined surface, thus enhancing its ability to reflect contact with a surface from the slave back to the master. The invention can further comprise a tremor filter. The invention can further comprise means for compensating for gravity. The invention can further comprise means for recording and playing back motion commands.

The method of the present invention for micromanipulation comprises the steps of providing a master dual planar structure with a coordinated X and Y and orientational output, providing a slave dual planar structure comprising a second coordinated X and Y and orientational output and mimicking and scaling down the first coordinated X and Y and orientational output to the second coordinated X and Y orientational output. The method further comprises the step of moving a first gimbaled arm affixed to the master dual planar structure along an axis of the first gimbaled arm and mimicking and scaling the movement along an axis of a second gimbaled arm affixed to the slave dual planar structure. The method further comprises rotating the first gimbaled arm about its axis and mimicking and scaling the rotation along an axis of the second gimbaled arm. The step of mimicking comprises providing push—push apparatuses. The step of scaling comprises providing a computer. The method further comprises the step of feeding back a signal from the second gimbaled arm to the first gimbaled arm when the second gimbaled arm contacts a predetermined surface. The method further comprises the step of filtering tremors. The method further comprises the step of compensating for gravity. The method further comprises the step of recording and playing back motion commands.

The novel features of the present invention will become apparent to those of skill in the art upon examination of the following detailed description of the invention or can be learned by practice of the present invention. It should be understood, however, that the detailed description of the invention and the specific examples presented, while indicating certain embodiments of the present invention, are provided for illustration purposes only because various changes and modifications within the spirit and scope of the invention will become apparent to those of skill in the art from the detailed description of the invention and claims that follow.

BRIEF DESCRIPTION OF THE DRAWINGS

The accompanying figures, in which like reference numerals refer to identical or functionally similar elements throughout the separate views and which are incorporated in and form part of the specification, further illustrate the present invention and, together with the detailed description of the invention, serve to explain the principles of the present invention.

DETAILED DESCRIPTION OF THE INVENTION

Figure 1:
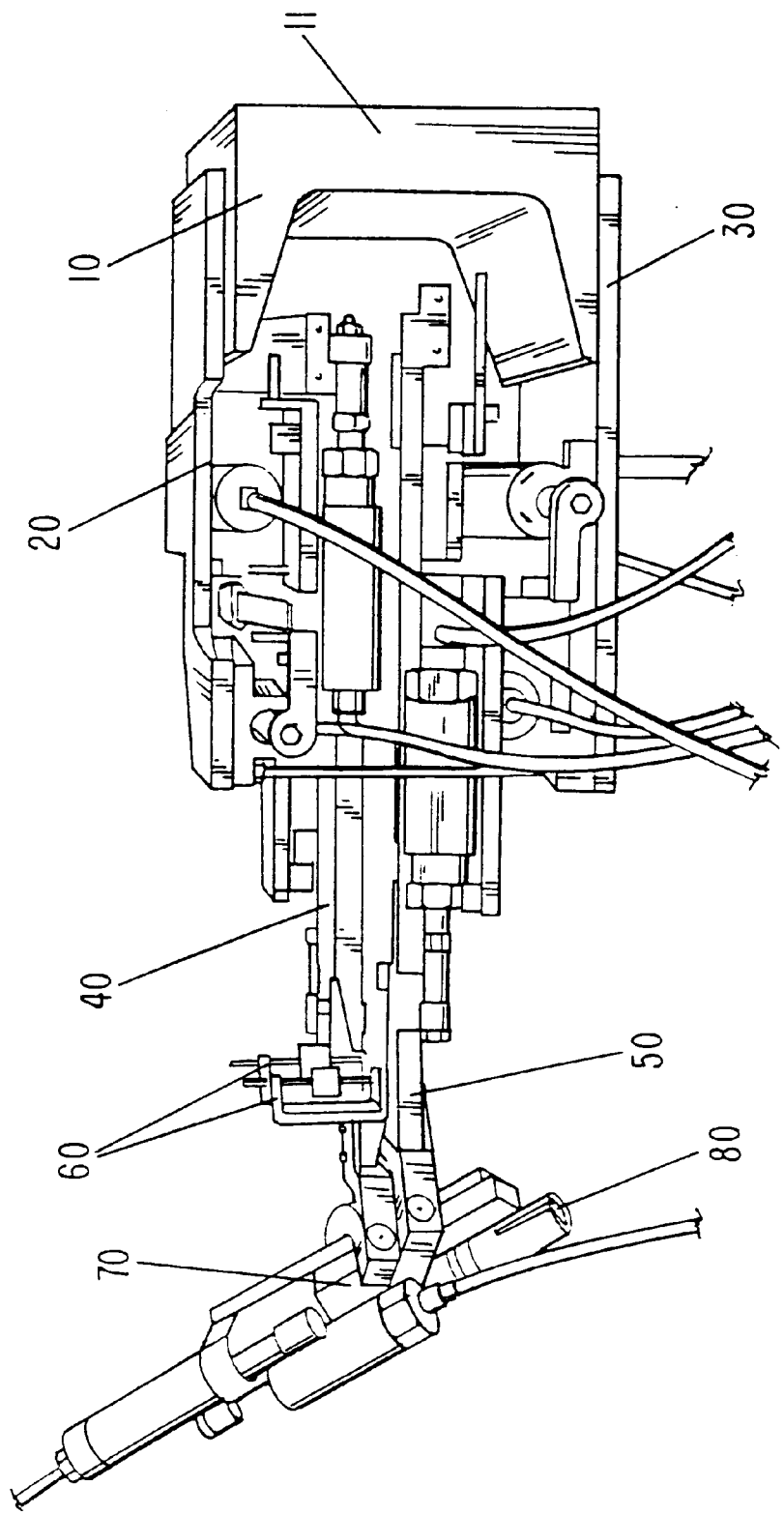
FIG. 1 is a side view of an embodiment of the present invention.

The overall design of the platform of the present invention is based on the theory that very precise X-Y stages, which are used in many precision applications, such as laser aiming and directing systems X-Y stages that are used for micro positioning stages, can present a basis for precision motion in six degrees of freedom.

The present invention combines a six degree of freedom platform with a computer, programmed with software, that connects to another six degree of freedom platform. The first platform can be used as a joystick, with four sensors built into each of the axes, and the second platform responds to commands provided by the first platform. In other words, the user has his/her hands on the end of a sixth joint on the first system, or master, and he/she is moving the system, thus back driving the motors. The system senses the position and forces at each joint that are imposed by pushing on it. A signal is sent to the computer, the computer takes the force and displacement numbers and sends them to the second system, which is called the slave system. The master system commands motion of the motors in the second system in order to generate motion that basically mimics the first system. This is more commonly known as a master-slave arrangement. If the slave system contacts a surface, then it too has positive force sensors that sense the position and forces. The position and forces are sent through the computer back to the master system. The motors in the master system are commanded to move and drive against the hand of the person who is holding the device, indicating that contact had been made. This is called force reflection or force reflecting tele-operation. Some of the unique features of the present invention are the mechanical platform, which relies on very precise technology in a very unique arrangement, and a very unique architecture for control, which provides a very high bandwidth operation. Current open architecture software control technology (e.g., commercially-available software from Delta Tau, Trellis, and Galil Motion Control) is capable of controlling the robot system in a position-controlled autonomous environment. (Delta Tau is the name of a company that sells control solutions for different types of applications; Delta Tau offers the preferable commercially-available system. Delta Tau is located at 9036 Winnetka Avenue, Northridge, Calif. 91324. Trellis Software & Controls, Inc., is located at 2619 Product Drive, Suite 106, Rochester Hills, Mich. 48309-3807, a company that was recently purchased by Hewlett Packard. Galil Motion Control is located at 575 Maude Court, Sunnyvale, Calif. 94086.) The disadvantage in using current open architecture software is that this application is not just a true autonomous problem. Ideally, external software must be written to integrate platforms such as these to operate in a master/slave arrangement. Thus, in order to use a typical motion control board available on the open commercial market, additional external computing and control is necessary for these systems to operate in the environment described. The optimum software configuration for this application is to tightly couple the control systems of the master/slave devices on board a high-performance computing environment. Some algorithms run as high as 5000 Hertz to provide smooth, torque ripple-free motion, while others run at half of the above rate. This type of performance is not possible with generic open architecture controllers without some modifications.

The unique hardware design for the structural elements is comprised of two planar actuator sets. One X-Y controlled plane is situated on top of a second planar X-Y controlled set, which is referred to as a dual planar design. This dual planar design can be visualized by taking both hands and arranging them together with palms facing each other, spaced a small distance apart and slipping a pencil between the fingers of each palm, so that they are interconnected through this pencil. As one moves his/her palms in planar motion relative to each other, in any direction, the pencil motion is controlled. The pencil moves in rotation if the palms are moved in opposite directions or movies linearly if the palms move in the same direction or some variation thereof in order to achieve coordinated motion of the pencil. If the tip of the pencil is placed on a piece of paper, then a drawing is made when the tip changes orientation and position relative to the positions of each of the two planes (two palms). This would be the top plane and the bottom plane. For each plane, there is an X-Y control; the top plane has an X-Y control and the bottom plane also has an X-Y control. The stages can be positioned. The top stage and the bottom stage move throughout their individual ranges of motion, X and Y, precisely because of motors and encoders, that are provided on each of the X and Y stages, individually. The top plane represents two axes (X and Y), the bottom plane represents two more axes (X and Y), adding up to four axes, generating four degrees of freedom. Figuratively, the pencil connects those two planes through a set of two two-axis gimbals. Motion along the axis of the pencil and rotation about the axis of the pencil generates the fifth and sixth degrees of freedom. Therefore, a total of six degrees of freedom is made up by two X-Y planes which are four degrees of freedom and two more degrees of freedom which are generated by moving in and out along the axis of the figurative pencil and around its axis, rotation-wise. This is a very unique design for six degrees of freedom.

With this design, one can achieve a minimum of ten microns resolution at the end of the last joint which is the sixth joint. Applications can be realized in many things that need and require precise motion. Precise motion is needed, for example, in surgery, micro-surgery in particular, eye surgery, vitreo-retinal surgery, ear, nose and throat surgery, neurosurgery, micro-hand surgery or micro-orthopedic surgery, in general, or any surgery that require microscopes. In essence, the present invention provides tools similar to those provided by a microscope. A microscope provides the ability to magnify a view of something that is very small. The present invention provides basically the opposite; it allows motion that is generated on the order of millimeters in one's hand to be down scaled to produce micron motions on the work surface, which allows translation of hand motions in millimeter space to micron motions within the microscope space. To extend the applications, the present invention can be used in applications such as microelectronics assembly, microelectro-mechanical systems (MEMS) assembly for micron scale gears, motors, and the like. Several companies are generating MEMS devices using standard electronic fabrication techniques, however, there are very few methods for actually assembling these devices once they are manufactured.

The present invention allows a user to down scale motions and because this system is controlled via computer, it also allows the application of filters for anomalies such as tremors. Most individuals experience a tremor to some level. If, for example, the operator or surgeon has a tremor that is due to some neuromuscular limitations, the present invention allows filtration of such a tremor if the frequency of the tremor can be characterized.

FIG. 1 shows an overall side view of an embodiment of the present invention. The micromanipulator shown has a duplicate set of X and Y planar structures, top plane control arm 40, also referred to herein as Y control arm 40, and bottom plane control arm 50 attached to two long arms which are combined with a gimbal system. Attached to the gimbal are joint five 70 and joint six 80, which will be discussed in detail below.

Figure 2:
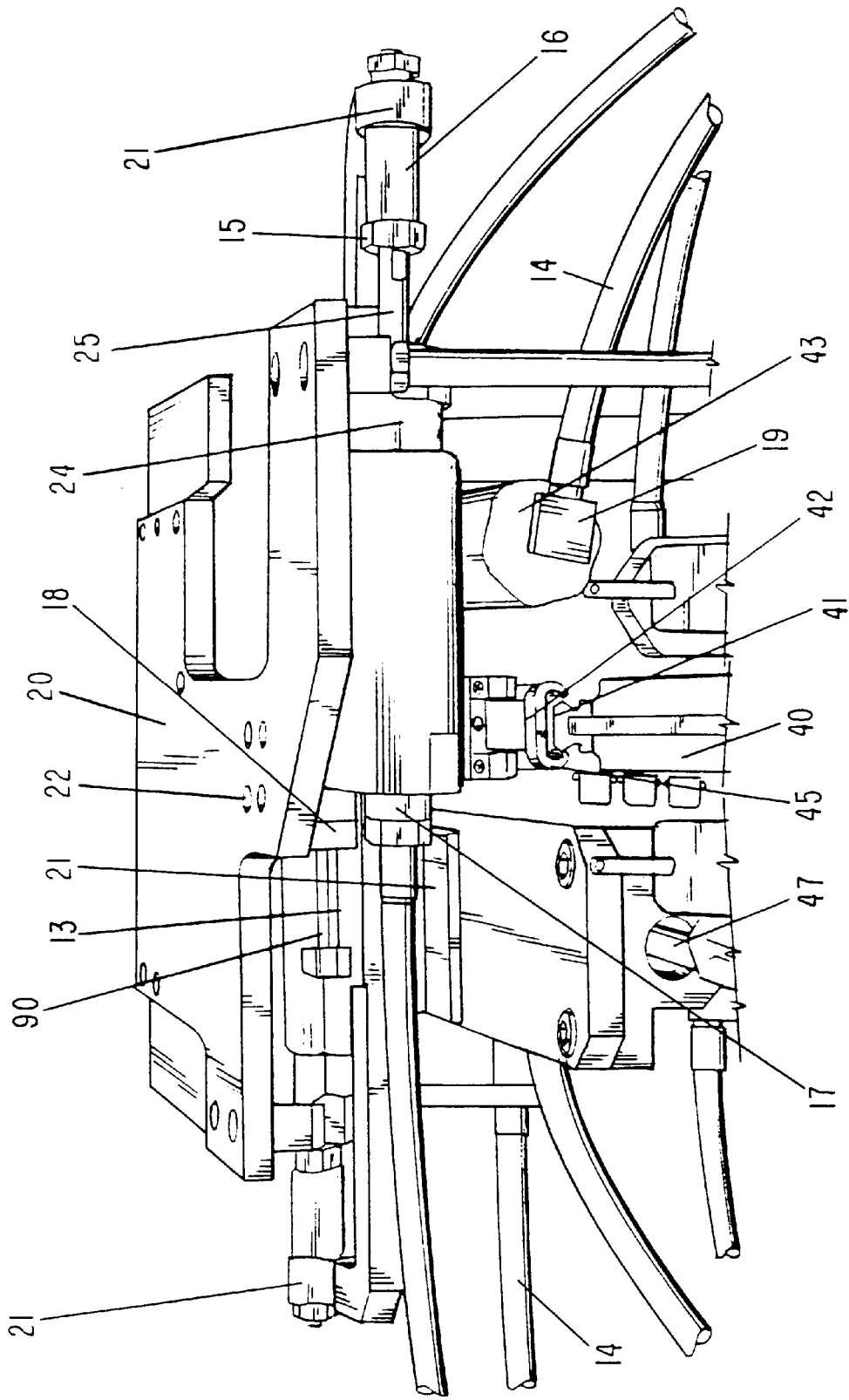
FIG. 2 is a front view of the top stage of the present invention of FIG. 1.
Figure 3:
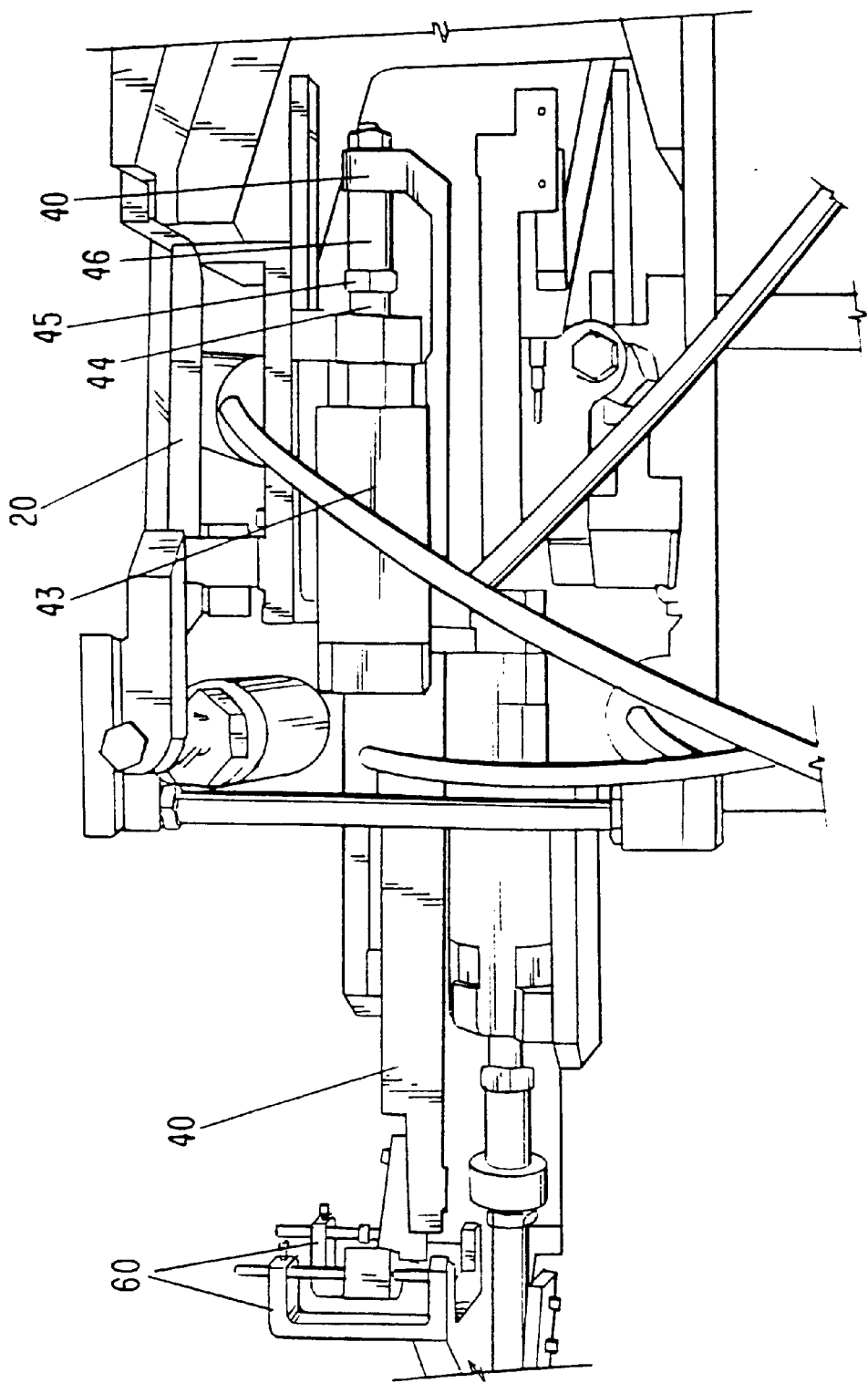
FIG. 3 is a view of the top stage.

Base frame 10 has a U frame shape on its side with top portion 20, bottom portion 30, and back part 11. Top X-Y plane control arm 40 is attached to top portion 20, and bottom X-Y plane control arm 50 is attached to bottom portion 30, as shown. Two plane control arms 40 and 50 extend from each of the X-Y planes. Top plane control arm 40 is attached to bottom plane control arm 50. Each plane control arm 40 and 50 can move in X and Y directions individually and independently. Top plane float 60 is affixed as shown in FIGS. 1 and 3. As in the previous analogy, if one has his/her hands together with fingers interlocked on the pencil so the pencil cannot slip in and out, the hands are spaced at a certain distance when the pencil is perpendicular to the plane of the hands. As one's hands are moved in opposite directions with respect to each other so that the pencil is no longer perpendicular, the hands approach each other. Similarly, as top plane control arm 40 moves in an opposite direction with respect to bottom plane control arm 50, top plane float 60 allows for the change in distance between the planes. This is needed to achieve various angles of orientation of joint five 70 and joint six 80. The gimbal arrangement will be described later. The present invention is ideally suited to be configured as a hydraulically-controlled system. Hydraulic hoses (or tubes) 14 provide water to the system as shown in FIG. 2. Other configurations can be utilized, such as direct drive motors, screws that drive, based on rotary motors, or other linear actuator systems that deliver very precise motion such as lead screws, ball screws which provide linear motion while also providing back driveability, or linear motors directly driving the system. The present invention can utilize Bellofram diaphragms, which are rolling edge diaphragms, or bellows which are similar to hydraulic cylinders. Hydraulic piston and sleeve cylinders can also be used. To minimize the size of the total package, the motors can be removed into a separate unit and connected to hydraulic lines.

Figure 9:
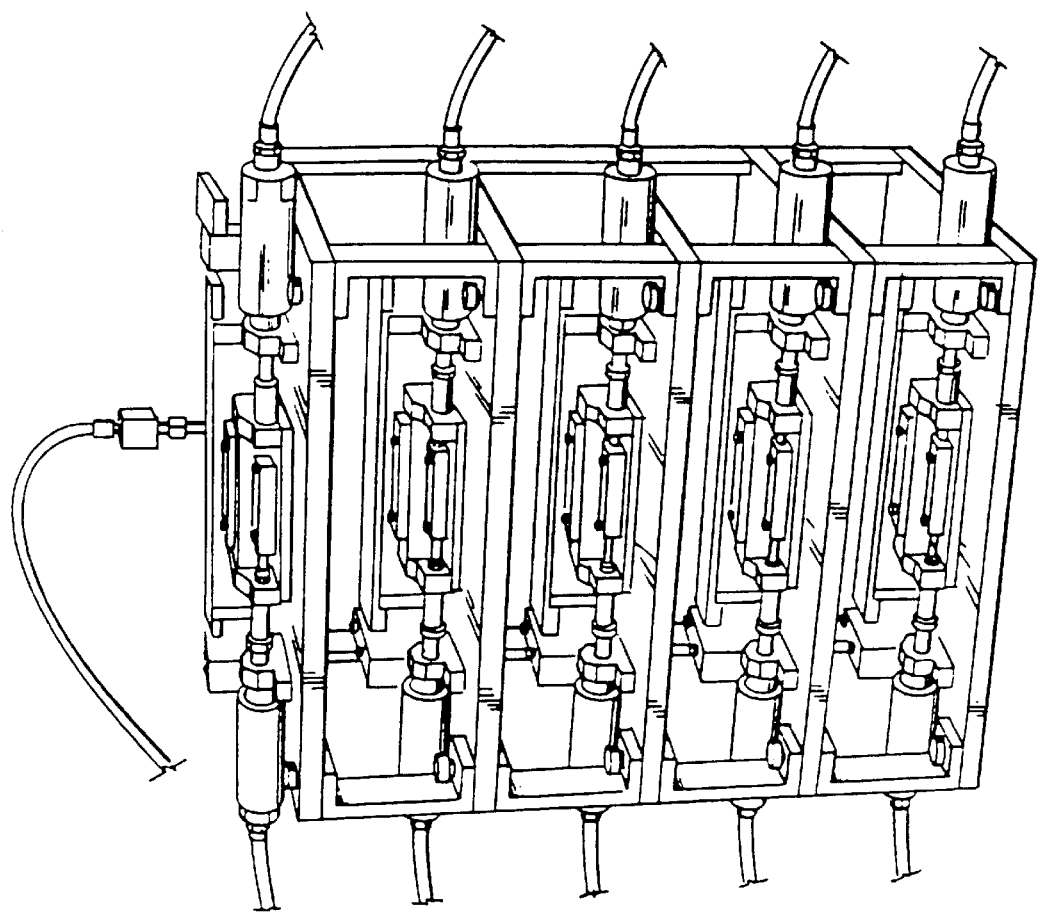
FIG. 9 illustrates the drive train.

FIG. 2 shows a front view of the top stage or top plane of the system. Top portion of base plate 20 is shown attached to base frame 10. Affixed to top portion of base plate 20 is X axis bearing 13 which is a linear bearing that can be a recirculating linear ball bearing or a recirculating cross roller bearing, or any type of bearing with very high precision and which can take high moments. The linear bearing used in the embodiment shown is a linear ball bearing manufactured by THK. X axis bearing 13 is attached to pillow block 18 which is attached to top portion of base frame 20 with four pillow block screws 22. X axis bearing 13 attaches to X axis bearing rail 90, to control arm 21 as shown. This allows control arm 21 to move in the X direction relative to the top portion of base frame 20 which is stationary. Control arm 21 is attached to two X Belloframs 24. The outside cylinder of X Bellofram 24 is shown with an extending center piston 25 attached by hexagonal nut 15 and spacer 16 to control arm 21 as shown. Hydraulic hose 14 is attached to fitting 17 on the back of X Bellofram 24 in order to deliver the water fluid. There is a duplicate X Bellofram 24 configuration in the rear part (not shown) of view of FIG. 2. The reason for these two Bellofram configurations is to act in opposition to each other in order to provide X motion. The one cylinder pushes to generate leftward motion and the other cylinder pushes to generate rightward motion. This is duplicated on the control drive train, as shown in FIG. 9. Pairs of Belloframs that are pushed in opposite directions in order to generate push—push type motion. This entire arrangement relies on compression of fluid and does not rely on pulling of the fluid.

A second linear Y axis bearing 41 is attached to control arm 21 with the same arrangement as described before with pillow block 45 which is attached to control arm 21 and rail 41 which is attached through screws 42 to top control arm 40. The previously described Bellofram drive is a duplicate of the aforementioned arrangement. See Y Bellofram 43. Due to the aforementioned configuration, control arms 21 and 40 provide two stages of series X and Y motion. Rod 47 is shown extending outward from the view and provides outward motion. Hydraulic hose 14 is attached to a right angle fitting 19 to provide coupling between the drive train, in FIG. 9, and Y Bellofram 43.

FIG. 3 shows a side view of the present invention. FIG. 3 provides a view of rearward Y Bellofram 43. Pointed in a rearward direction are Y cylinder arm 44, Y hexagonal nut 45, and Y spacer 46, which are attached to the top control arm 40. Top control arm 40 is attached to top plane float 60 and to gimbal (not shown). The bottom plane control arm 50 of FIG. 1 is a mirror image of the top plane control arm 40 as heretofore described. Bottom plane structure is affixed to bottom portion of base frame 30 as shown in FIG. 1. Therefore, there are two X-Y planes, comprising top plane control arm 40 and bottom plane control arm 50, as shown in FIG. 1, affixed to two sets of gimbals.

Figure 4:
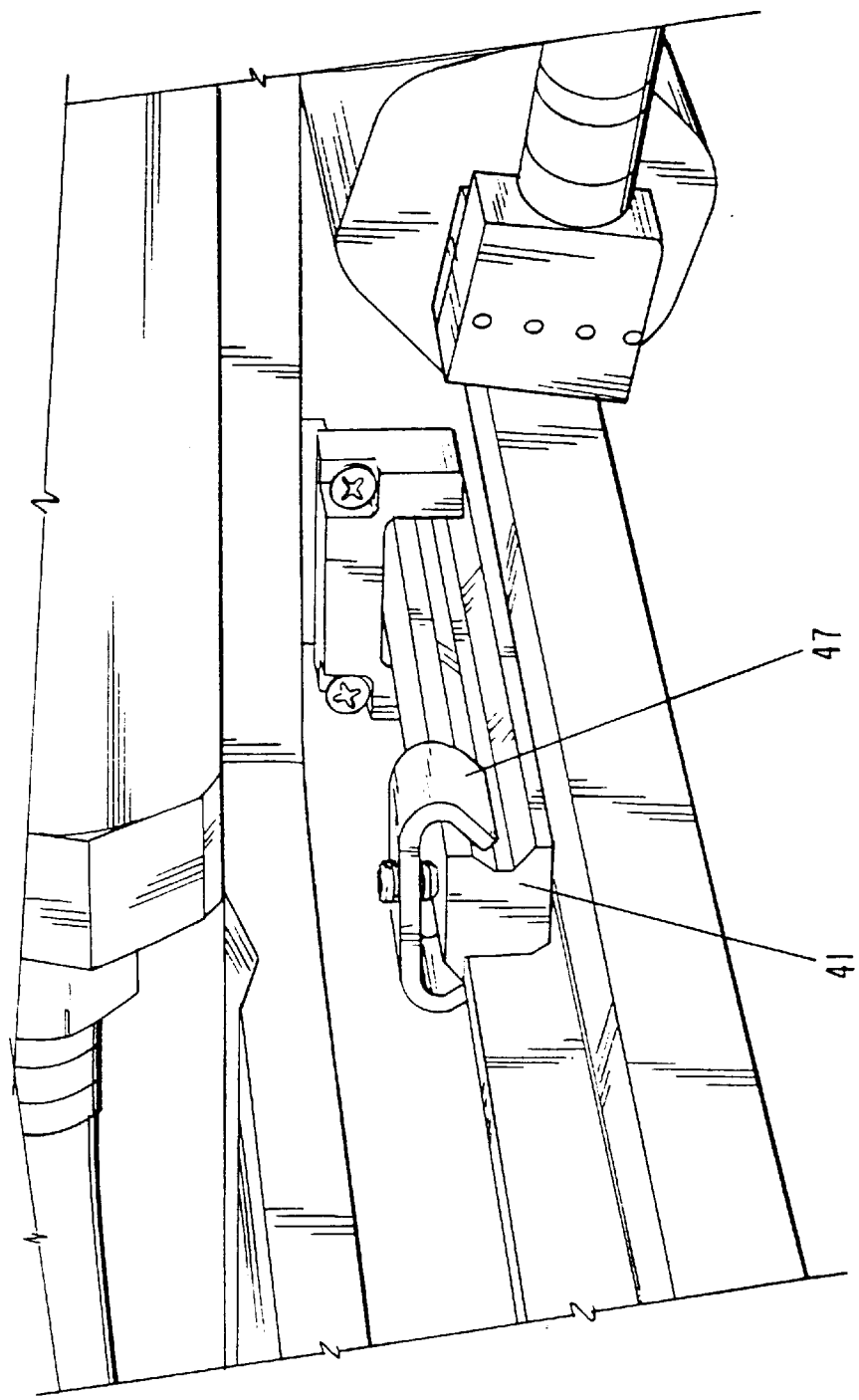
FIG. 4 is a perspective view of the Y axis bearing.

FIG. 4 shows a close-up of Y axis bearing 41 that is shown in FIG. 2. There is a stop block 47 attached to Y axis bearing 41, as shown in FIG. 4, that prevents over travel.

Figure 5:
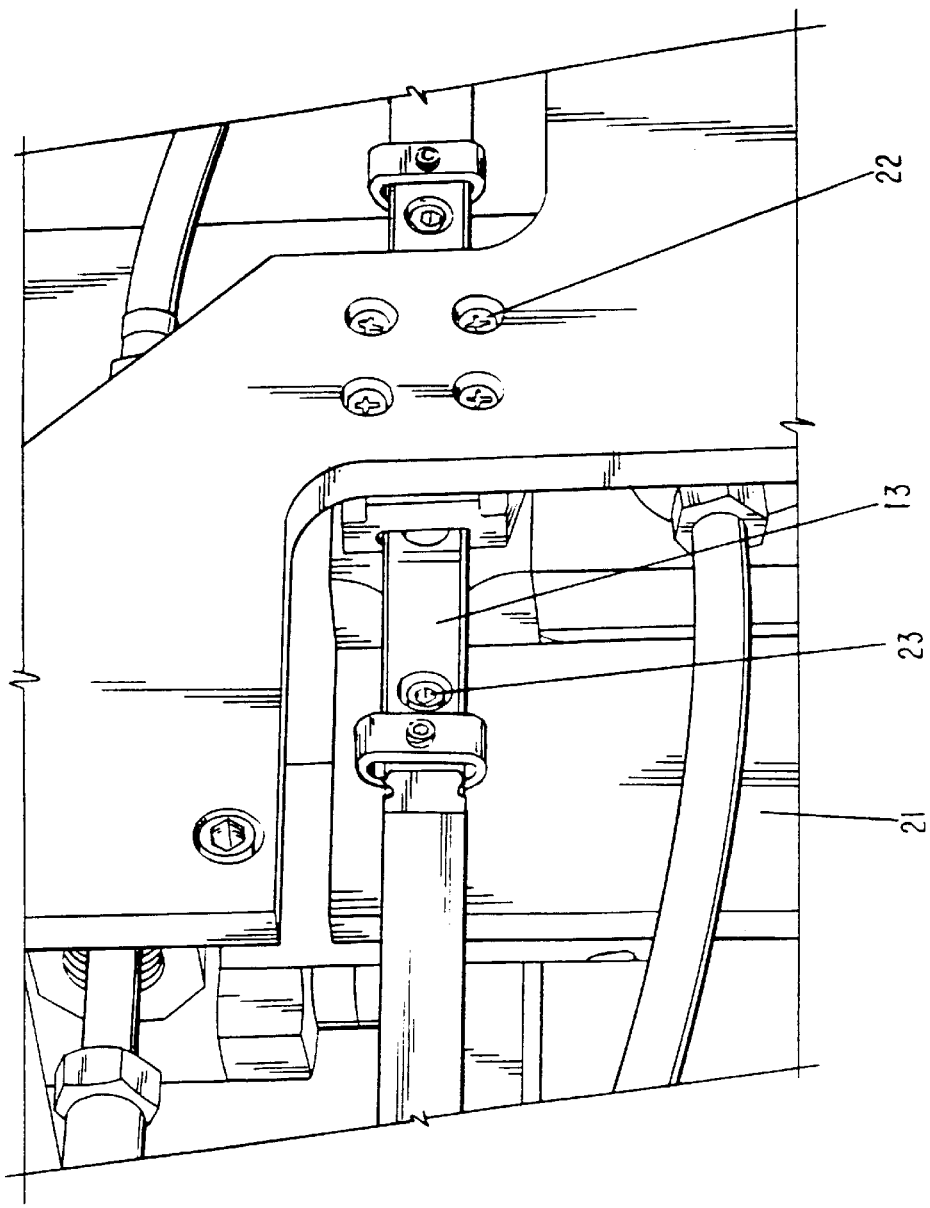
FIG. 5 is a perspective view of the X axis bearing.

FIG. 5 shows a close-up view of X axis bearing 13 that is shown in FIG. 2. Pillow block screws 22 attach pillow block of X axis bearing 13 and rail of X axis bearing 13 is attached with X axis bearing screws 23 to control arm 21 as shown in FIGS. 2 and 5.

Figure 6:
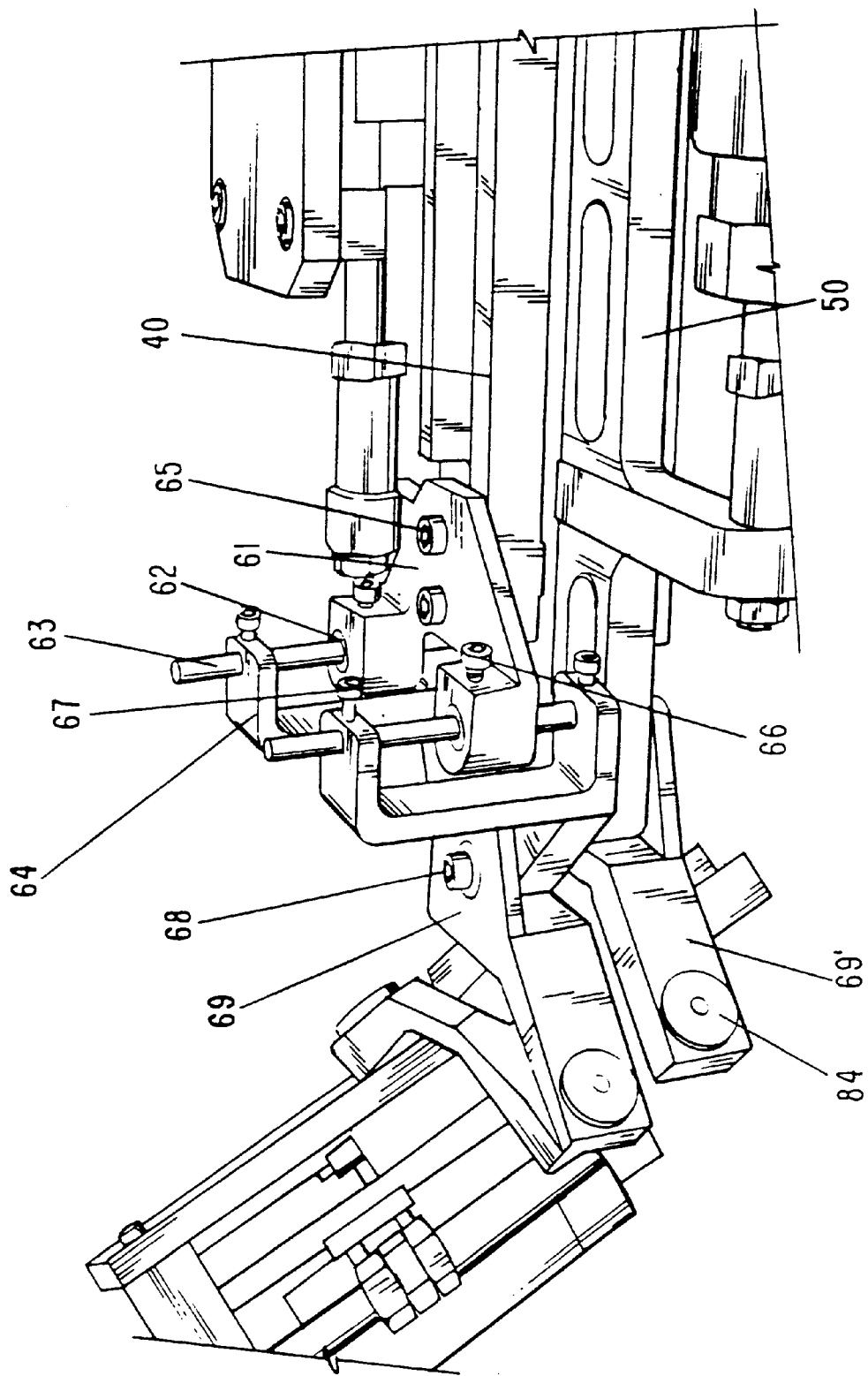
FIG. 6 is a view of the top plane float.

FIG. 6 shows a close-up of top plane float 60 that is shown in FIG. 1. Top plane control arm 40 and bottom plane control arm 50 control X and Y linear motions. FIG. 6 is a close-up view of the top plane float 60 comprising top plane bracket 61 which is attached to top plane control arm 40 with top plane bracket screws 65. Top plane bracket 61 houses linear ball bearing 62 which glides on bearing rod 63. Ball bearing 62 is attached to top plane bracket 61 with bearing screw 66. Bearing rod 63 is attached to end bracket 64 with rod screw 67. End bracket 64 is attached to gimbal bracket 69 with gimbal screw 68.

Figure 7:
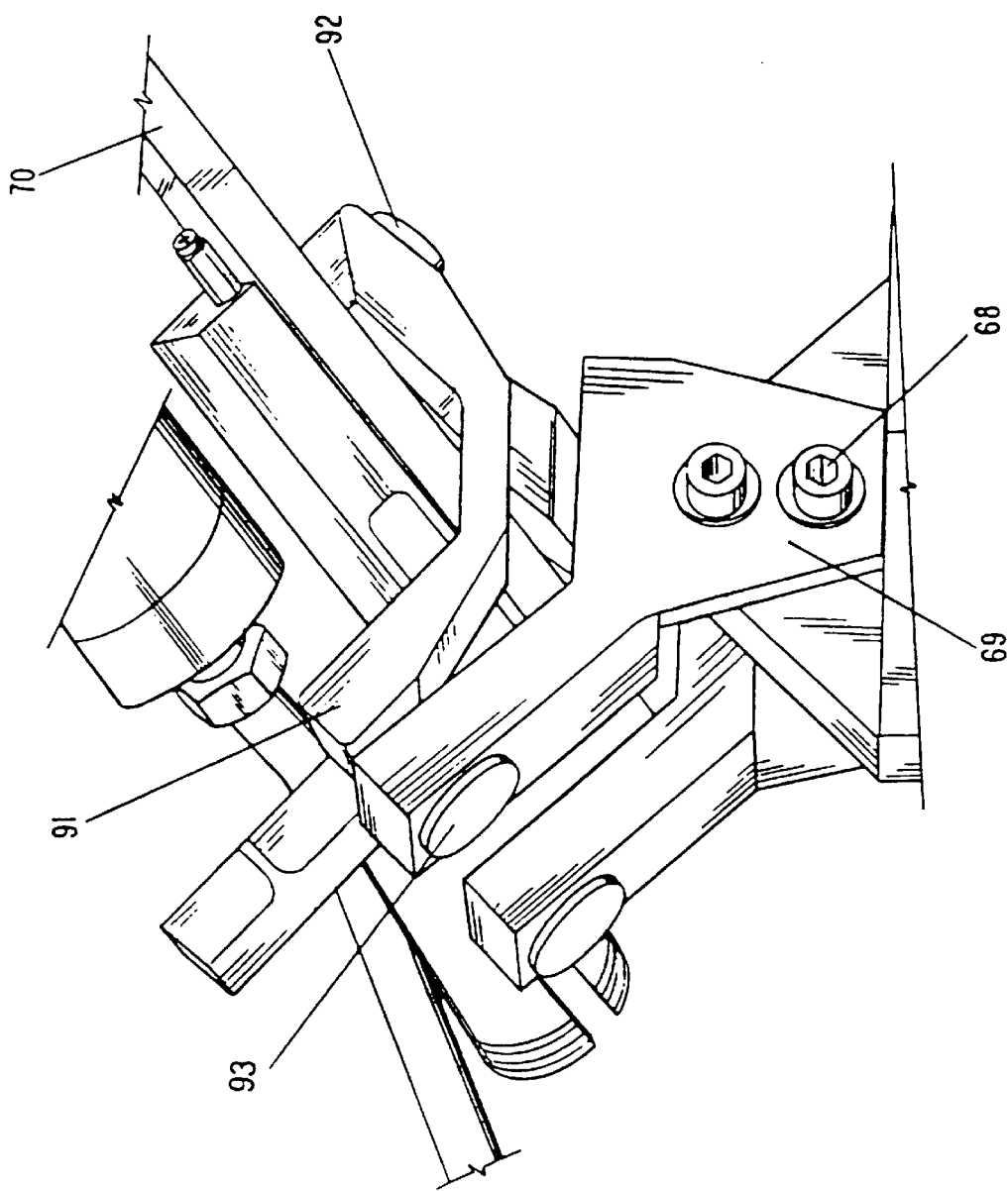
FIG. 7 is a side view of the dual two axis gimbals.

FIG. 7 shows a close-up view of the dual two-axis gimbals shown by gimbal brackets 69 and 69' of FIG. 6. Gimbal bracket 69 is affixed by gimbal screws 68. X axis bearing assembly 93 is a bearing which is housed in a bearing pocket in gimbal bracket 69, and there is a central bolt which runs through the inner-race of the rotary bearing which has a stop nut as shown. Again, the mirror bearing assemblies define two axes as shown in FIG. 7. The end gimbal arm 91 attaches to bearing assembly post of X axis bearing assembly 93 with a set screw in end gimbal arm 91. The end bearing assembly 92, which is a duplicate of the X axis bearing assembly 93, and the post of the end bearing 92 attaches to joint five 70, through a set screw in the body of joint five 70.

Figure 8:
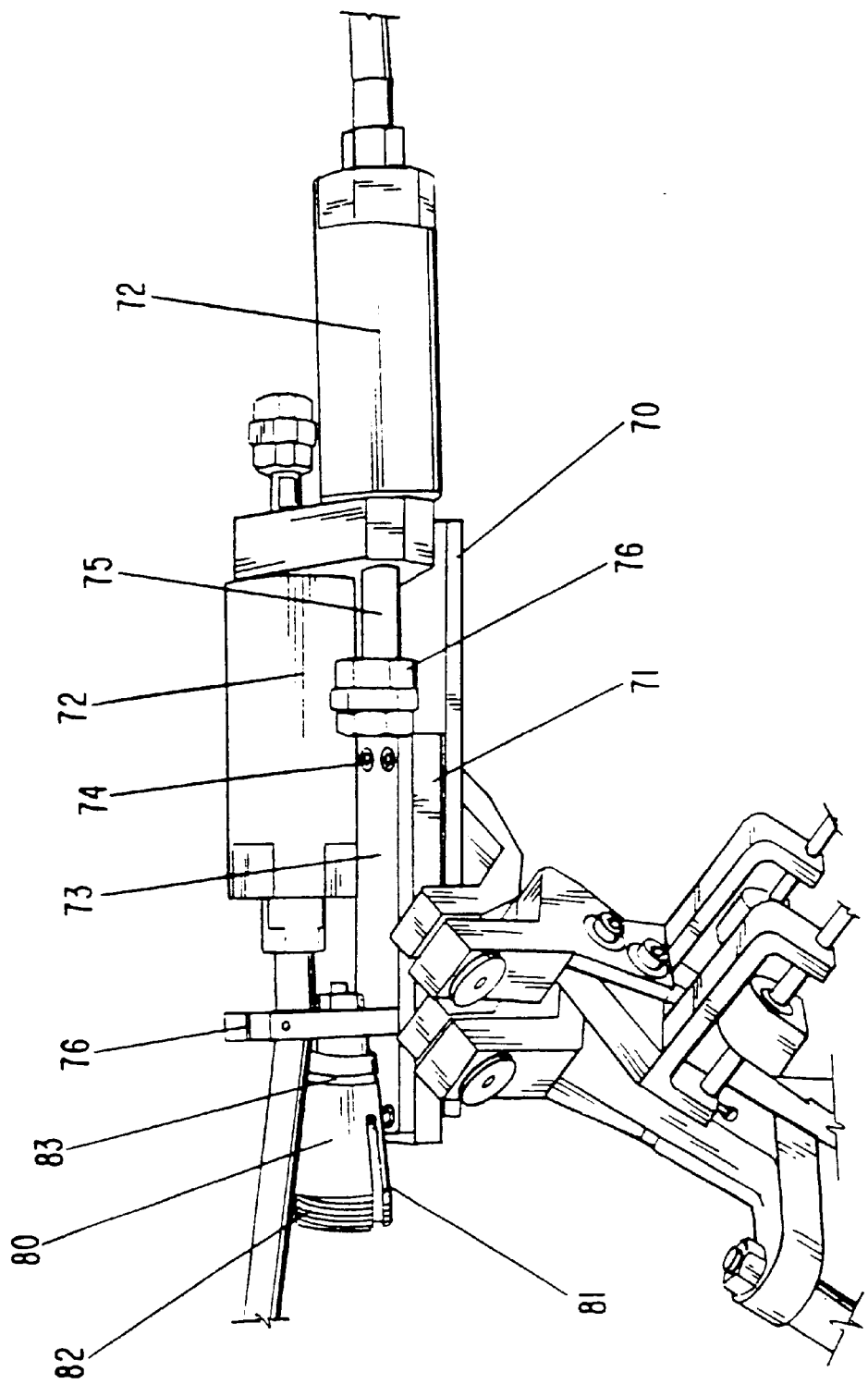
FIG. 8 is a side view of joint five and joint six without the motor.

FIG. 8 shows joint five 70 and joint six 80 without the motor. Base plate of joint five 70 is attached to linear bearing 71, rail of joint five linear bearing (not shown), is attached to base plate of joint five 70 with joint five linear bearing screws (not shown). The body of joint five linear bearing 71 is attached to joint five Bellofram cylinders 72 through mounting plate 73, which is attached with joint five linear bearing screws 74, which is then attached to the center rod of the joint five Bellofram cylinder 75. Joint five locking nut 76; locks the center rod of joint five Bellofram cylinder 75 in place. Again, there are two cylinders working in opposition in order to provide push—push motion for joint five 70. Top gimbal bracket 69 and bottom gimbal 84 are shown in FIG. 6. Top gimbal bracket 69 attaches to top plane control arm 40 and bottom gimbal bracket 69' attaches to bottom plane control arm 50.

Joint six 80 of the system is shown in FIG. 8. Joint six 80 is not complete in this view. Joint six 80 is a housing for a tool comprising a clamp with a slot 81, as shown. There are threads 82 which mate with a lock nut (not shown). Provided is a groove for an O-ring belt drive 83. Joint six 80 is mounted to mounting bracket 76 through a bearing. Joint six bracket with clamp 76 is attached to mounting plate 73, as shown. Joint six bracket with clamp 76 can clamp the end of the motor with a pulley at the end of that motor shaft (not shown). Within that pulley would be attached the O-ring that would drive and mate up with O-ring belt drive 83 and provide rotational motion.

Figure 10:
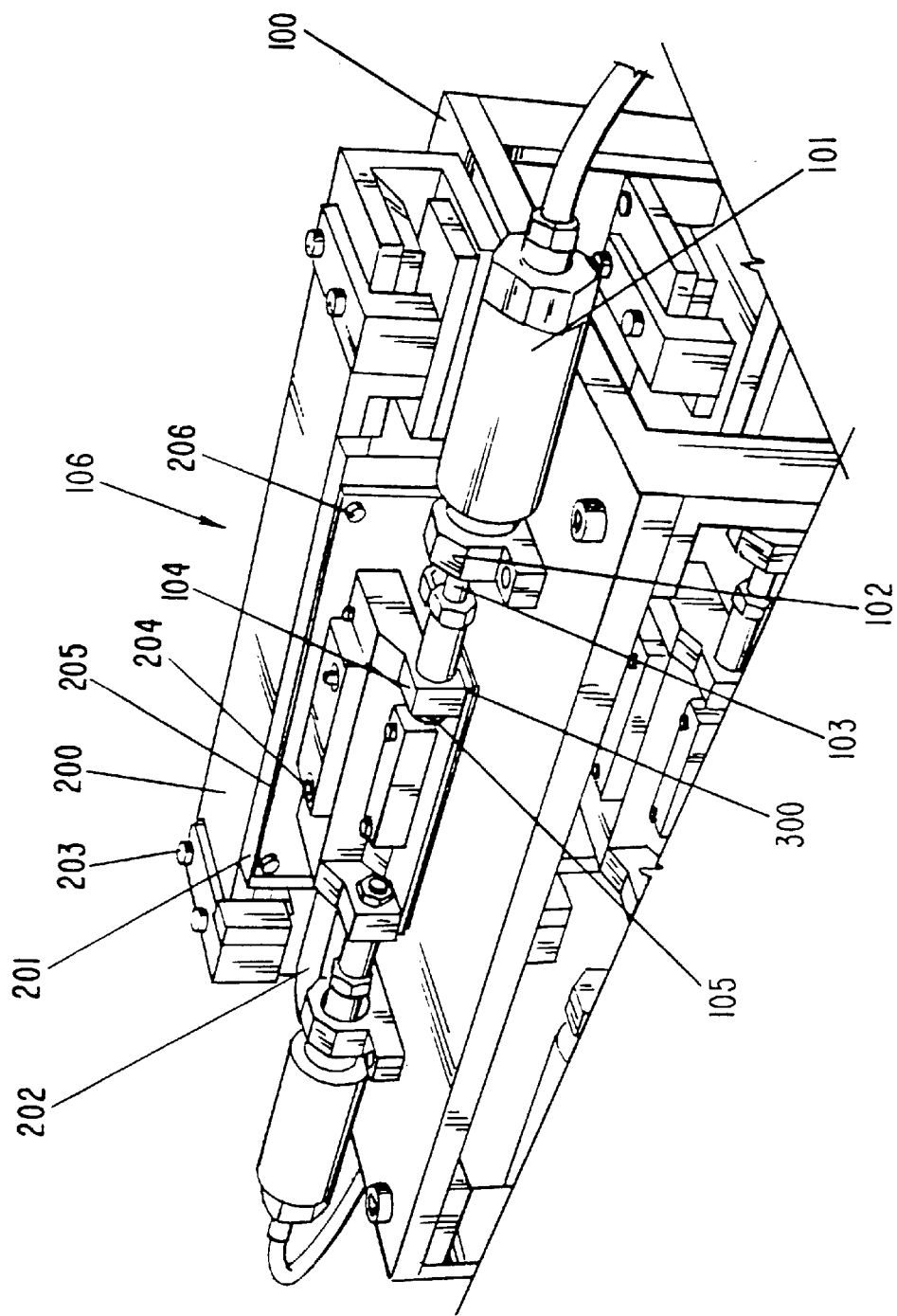
FIG. 10 show a single stage of the drive train.

FIG. 9 is an overview of the drive train. There are five identical stages of push—push cylinders. Again, the Bellofram cylinders are stacked together. A close-up view of this drive train, showing one stage—the top stage— is shown in FIG. 10. Base plate for top stage 100 is shown. Top stage Bellofram 101 is mounted to base plate for top stage 100 through foot mounting device 102. 22 Rod of top stage Bellofram 103 is attached to spacer and motor mount 104, and tightened down with center rod nuts 105. It is noted that there is a complimentary Bellofram configuration on the aft side of the stage. The motor 106 is made up of two portions, magnet portion 200 and moving coil 201. Moving coil 201 moves back and forth in the gap of magnet portion 200, as any conventional linear motor would move. Cable 202 delivers the voltage and current required to move coil 201 back and forth. Any motor can be used in this case, such as a linear motor, ball screw, lead screw, rotary motor, or the like, in order to provide linear motion. There is an encoder 300, attached as shown, which provides for very precise quarter micron resolution positioning. An encoder 300 suitable for use in the present invention is available from Micro E Devices. In this particular case, this is an optical device using a laser system. Magnet portion 200 is attached to base plate 100 via magnet attaching screws 203. Motor mount 104 is attached to moving coil 201 through coil screws 204 to moving coil plate 205. Finally, moving coil plate 205 is attached to moving coil 201 via plate screws 206.

This arrangement is duplicated for the each of the five axes going out to end rotary joint which is provided by a motor at the end, or joint six 80. These all stacked together as shown in the overview of the drive train in FIG. 9.

Figure 11:
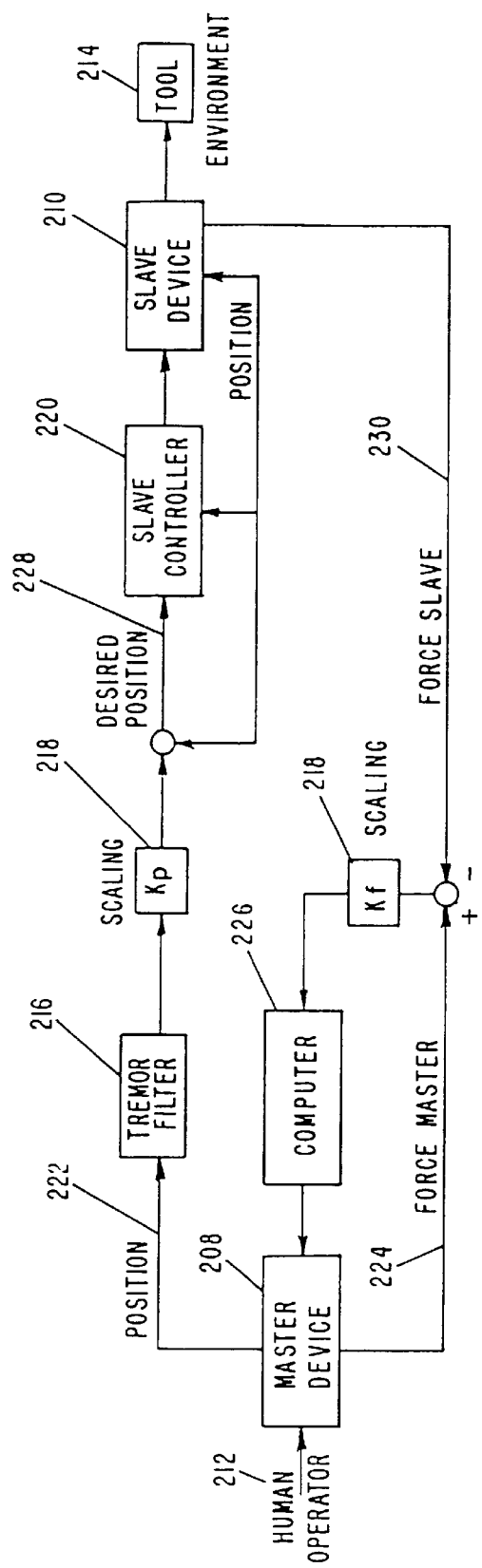
FIG. 11 is a block diagram of the overall system of the present invention.
Figure 12:
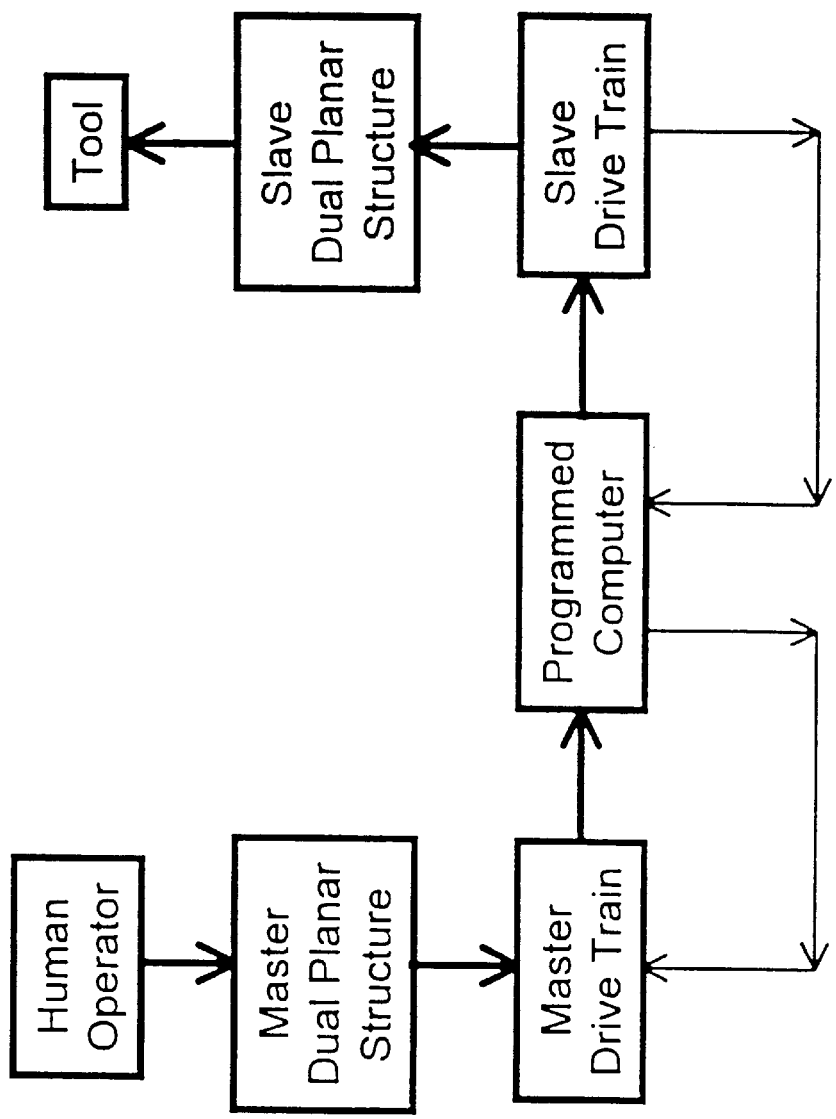
FIG. 12 illustrates the combination of the X-Y stage apparatus and drive train structure.

The present invention can be used for surgical procedures, as a micro-assembly tool, or the like. FIG. 11 is a block diagram of the master-slave system. There are two main parts of the master-slave system, the master 208 and the slave 210, which work together. Master 208 is grasped at the end of joint six 80, as is shown in FIG. 1 by human operator 212. There is a tool 214 attached to the holder at the end of joint six 80 of the slave 210. Tool 214 can be anything from small grippers to surgical tools, like microvitrectomy tools for eye surgery, very small shavers and cutters, and tools that are used for ear, nose and throat surgeries, or other similar devices. When tool 214 is used, it is placed on the end of slave 210. Master 208 has a handle that sticks out of the tool holder, such as a rod that the user holds onto. As the operator, whether a surgeon or someone in a microelectronics fabrication facility, moves the end of joint six 80, the movement back drives the motors, which cause the encoders to read different positions 222 in each of the motor joints and they also impart force onto the structure which is sensed by the force sensors 224 within the structure. The force sensors 224 and the encoders act to send signals to the computer 226, which then reads those values and applies various filtering by filter 216, gain, adjustments to either increase or decrease scaling 218 of those values, and sends the enhanced signals to the slave controller 220 that drives the slave 210. The signals, which are in the form of voltages, instruct the amplifiers that drive the motors for the slave to move in a certain direction. Slave 210 also has a set of slave encoders 228 and slave force sensors 230. As it is commanded to move, it will interact with its environment, whether it be hardware for microelectronics or for surgical patients, it will sense any kind of contact forces. When it does so, it will again send a signal back to the computer 226 as described before, which is then reflected back to the operator 212. The motors for the master device are driven by the scaled signals and the operator then senses contact with a hard surface, such as a bone or a microelectronics part. An important part of being able to operate in a microscopic environment is using a microscope. This entire apparatus will be used under a microscope so that the operator can see down to the micron scale and view the motions. The operator 212 can control the motions in a correct direction to prevent collisions and provide proper motion. The computer 226 not only translates signals from master to slave and slave to master, but also coordinates the joints of each of the master and slave. There are kinematic and dynamic models loaded into the computer 226 that stabilizes the system and also provides coordinated six degree of freedom motion. So discussed previously, a circle drawn on a page requires coordinated kinematic transformation matrices that are part of controller.

When a hydraulic design is used in the present invention, it is arranged such that the master and the slave apparatus is configured small enough so they do not obscure the work space for very small operations. If a doctor or fabricator is dealing with very small operations, then he/she desires not to have a very large apparatus sitting next to the patient and/or the microelectronics fabrication site. Therefore, the hydraulic system is designed to place the entire motor drive unit in a remote location. An example of Belloframs suitable for use in the present invention are commercially-available units by Bellofram, Inc. Company. However, in an alternative embodiment, the Belloframs can be in encased bellows. These bellows are closed off at one end and placed inside of a tube. The space between the bellows and the tube is filled with water and duplicates a Bellofram. A control rod would come out from the closed off end plate of the bellows and act to drive the system. The bellows also provide a spring force, which is sometimes disadvantageous because the spring action of the bellows would also give stored energy to the system which typically is not something desirous in a surgical platform, primarily because if the power goes off, spring force would then relax and could cause unexpected motion at the end of the tool. Belloframs in contrast are folded membranes that do not store energy in that fashion.

The present invention is a robot system, or motor servo controlled apparatus which is indirectly commanded by a computer. In this particular case, the motor servo controlled apparatus utilizes a master system so it is not computer controlled directly. The apparatus can be controlled by the computer to command position, velocity, and acceleration so that the user could pick up a part at one location and place it in another location all within a very small work space. The total work space of the robot system can be approximately a sphere with a diameter of 1.5 to 2 inches. The embodiment can be made of aluminum with metal bearings. The components can be made out of other known materials to either reduce weight or to potentially use the device within a magnetic environment, such as a magnetic resonance imaging (MRI) system. In this manner, a doctor could perform surgery while viewing inside the body of a patient.

The fluid within the hydraulic system can be water, oil, or other suitable fluids know to those of skill in the art. The master-slave arrangement can be a low pressure system similar to a car brake system but can be configured using hydraulic power units at higher pressures and using hydraulic servo valves to control the system. The Belloframs can be replaced/exchanged with hydraulic cylinders. However, hydraulic cylinders have high friction associated with them. When dealing with very small micron range force and positions, the system has to be designed to build up pressures to overcome the friction and then, once the friction is overcome, the device would noticeably jerk. Because the system has force sensor and position sensor or encoder, tremors within the operator's hands are sensed, characterized and removed from the system so that very smooth operating motion would be seen at the slave device as a commanded motion. Other things that the controller or computer system can provide are methods for controlling the maximum velocity and maximum acceleration systems so that the operator can move very quickly with his master but those motions would not be translated to the slave, necessarily, for safety purposes. Furthermore, other things that the controller or computer system can provide for are gravity compensation to enhance the dexterity of the operator. The software that operates the controller and provides motion commands to the manipulator should be programmed such that forces due to the effects of gravity on the robot and payload are completely compensated in all positions and orientations (translations and rotations), i.e., the device will be weightless. If the master is released by the operator without any breaks, regardless of load orientation, then the load will be supported and will not experience the forces of gravity (the forces of gravity become negligible). The operator will then experience less fatigue by not having to support the mass of the robot and payload, which will increase the precision of the operator during the procedure. Only forces from contact of the tool and the workpiece (e.g., human tissue) are reflected back to the master in the form of force feedback. The computer system can also be used to record all motions during a surgical operation and then played back to the master system with a recorded visual record for training purposes. A resident or intern (i.e., anyone less experienced) could look through a microscope and see the actual surgical procedure that occurred and also to be able to feel the motions that were imparted during the surgery. This would be similar to a fight simulator for training pilots or an automobile retrofitted with dual steering mechanisms for driver education. A means of recording are provided such that the command (motion) signals sent from the master are recorded so that manipulative tasks can be played back for subsequent use. The more experienced operator will use manipulator and play back the recorded commands for those in training; thus, the less experienced operators are allowed to experience the commands and motions experienced by the more experienced operator, which were recorded earlier in time. Any means of recording will suffice, including but not limited to the audio track of a video recorder, optical disk, digital video disk, CD-ROM, MOD, analog or digital tape, PCM tape, etc.

The computer system can also be used to operate the manipulator in a dual control mode: (1) first mode and (2) second (delta) mode. In the first mode, the expert performs the task at hand and the less experienced operator views the actions through some means. Two masters are used to control one robot. The motion commands are added (summed) with no weighting, which enables either of the two masters to assume control (both masters act to send motion commands). The masters are operated in a force reflecting or feedback manner. If one master moves, then the other master moves. In the second mode (delta mode), the less experienced operator performs the task at hand, while the more experienced operator is able to take corrective action to compensate for the actions taken by the less experienced operator. Any change or forces experienced by the less experienced operator are also felt by the more experienced operator, thus allowing the more experienced operator to compensate accordingly.

Examining a single axis of the system, there is a set of hydraulic cylinders arranged in a master-slave system similar to those found on automobile brakes. Driving the master cylinders is a servomotor which has connected to it encoders and force sensors, which can be pressure transducers that measure the pressure within the hydraulic line. The motor, master-slave cylinders with connecting fluid lines, and sensors make up a drive unit. Six drive units are used for the 6-DOF master, and six drive units are used for the 6-DOF slave. As the operator pushes on the hydraulic cylinder of the single axis, as an example, both forces and position displacement are sensed by the system. Those signals are sent to the computer, which then scales those values in appropriate manners to either down scale motions for the slave and/or change the force levels that are applied by the slave. The slave itself is controlled by the computer as well as a motor amplifier which senses the position and forces sensed by the slave. It is also provided with the command position and force information from the master. These command forces and positions are translated to voltages, sent to the motors for slave, slave motors then move to comply with the command values and the slave cylinder moves. If it contacts the surface within its environment then it corresponds to the action of the master, then it sends the force and position information back to the computer which then sends that information back to the master unit so that operator of the master unit can then sense what the slave unit is sensing. The present invention is a force reflecting master-slave manipulator. The slave is reflecting back the signals to the master and then to the operator, based on initial command positions and forces sent by the master. In a sense, it can be likened to a brake pedal in a car where a person will push in the brake of the car, the brake pads would clamp on the brakes of the car, and the forces of the clamping are sent back to the driver so that there is a sense of resistance associated with the brakes clamping down on the discs or the drum of the brake. Additionally, if the brakes of the car seize for some reason because of irregularities on the braking surface, these irregularities would be sent back to the pedal of the brake and would form vibrations which could be detected by the driver. An addition to this analogy in the present invention is a computer system that controls the motors.

Other variations and modifications of the present invention will be apparent to those of skill in the art, and it is the intent of the appended claims that such variations and modifications be covered. The particular values and configurations discussed above can be varied and are cited merely to illustrate a particular embodiment of the present invention and are not intended to limit the scope of the invention. It is contemplated that the use of the present invention can involve components having different characteristics as long as the principle is followed. It is intended that the scope of the present invention be defined by the claims appended hereto.

We claim:

1. A master-slave micromanipulator apparatus, comprising:
    a master dual planar structure, comprising:
    (a) a master frame;
    (b) a first master X-Y stage attached to said master frame;
    (c) means for moving said first master X-Y stage in both an X and a Y direction in a first X-Y plane relative to said master frame;
    (d) a second master X-Y stage attached to said master frame;
    (e) means for moving said second master X-Y stage in both an X and a Y direction in a second X-Y plane relative to said master frame, said second X-Y plane being oriented substantially parallel to, but not coincident with, said first X-Y plane;
    (f) means for generating a master coordinated X and Y and orientational output comprising a member connecting both said first master X-Y stage and said second master X-Y stage for coordinating motion of said first master X-Y stage with motion of said second master X-Y stage; and
    a slave dual planar structure, comprising:
    (g) a slave frame;
    (h) a first slave X-Y stage attached to said slave frame;
    (i) means for moving said first slave X-Y stage in both an X and a Y direction in a first X-Y plane relative to said slave frame;
    (j) a second slave X-Y stage attached to said slave frame;
    (k) means for moving said second slave X-Y stage in both an X and a Y direction in a second X-Y plane relative to said slave frame, said second X-Y plane being oriented substantially parallel to, but not coincident with, said first X-Y plane;
    (l) means for generating a slave coordinated X and Y and orientational output comprising a member connecting both said first slave X-Y stage and said second slave X-Y stage for coordinating motion of said first slave X-Y stage with motion of said second slave X-Y stage; and
    (m) means for mimicking and scaling said master coordinated X and Y and orientational output to said slave coordinated X and Y and orientational output.

2. The micromanipulator of claim 1, wherein said master dual planar structure comprises a first gimbaled arm and said slave dual planar structure comprises a second gimbaled arm.

3. The micromanipulator of claim 2, further comprising means for movement along an axis of said first gimbaled arm and said means for mimicking and said means for scaling further comprise mimicking and scaling said movement along an axis of said second gimbaled arm.

4. The micromanipulator of claim 3, further comprising means for rotation about the axis of said first gimbaled arm and said means for mimicking and said means for scaling further comprise mimicking and scaling said rotation along the axis of said second gimbaled arm.

5. The micromanipulator of claim 4, wherein said means for mimicking comprises push—push apparatuses.

6. The micromanipulator of claim 5, wherein said push—push apparatuses comprise hydraulic apparatuses.

7. The micromanipulator of claim 5, wherein said hydraulic apparatuses are selected from the group consisting of hydraulic piston and sleeve cylinders, rolling edge diagrams, and bellows.

8. The micromanipulator of claim 4, wherein said means for mimicking comprises a member selected from the group consisting of linear actuator systems, direct drive motors, drive screws, lead screws, ball screws, and combinations thereof.

9. The micromanipulator of claim 4, wherein said means for scaling comprises a programmed computer.

10. The micromanipulator of claim 2, further comprising a feedback loop for sending a signal from said second gimbaled arm to said first gimbaled arm when said second gimbaled arm contacts a surface.

11. The micromanipulator of claim 2, further comprising means for compensating for gravity forces experienced by the first gimbaled arm and the second gimbaled arm.

12. The micromanipulator of claim 1, further comprising a tremor filter positioned between said master dual planar structure and said slave dual planar structure.

13. The micromanipulator of claim 1, further comprising means for recording and playing back a plurality of commands exchanged between said master dual planar structure and said slave dual planar structure.

* * * * *